United States Patent [19]

Reilly et al.

[11] Patent Number: 4,677,980
[45] Date of Patent: Jul. 7, 1987

[54] ANGIOGRAPHIC INJECTOR AND ANGIOGRAPHIC SYRINGE FOR USE THEREWITH

[75] Inventors: David M. Reilly, Glenshaw; Arthur E. Uber, III, Pittsburgh, both of Pa.

[73] Assignee: Medrad, Inc., Pittsburgh, Pa.

[21] Appl. No.: 782,586

[22] Filed: Oct. 1, 1985

Related U.S. Application Data

[63] Continuation-in-part of Ser. No. 617,807, Jun. 6, 1984, abandoned.

[51] Int. Cl.⁴ .......................... A61M 5/20; A61B 6/00
[52] U.S. Cl. ............................. 128/655; 128/DIG. 1; 604/154; 604/228
[58] Field of Search ................ 128/654, 655, DIG. 1; 604/154, 155, 228, 197, 187, 232

[56] References Cited

U.S. PATENT DOCUMENTS

| | | | |
|---|---|---|---|
| 2,524,367 | 10/1950 | Smith | 604/228 |
| 2,637,576 | 5/1953 | Nottingham | |
| 2,702,547 | 2/1955 | Glass | 604/155 |
| 3,487,834 | 1/1970 | Smith et al. | 604/197 |
| 3,623,474 | 11/1971 | Heilman et al. | 604/655 |
| 4,006,736 | 2/1977 | Kranys et al. | 128/655 |

FOREIGN PATENT DOCUMENTS

| | | | |
|---|---|---|---|
| 2031841 | 1/1973 | Fed. Rep. of Germany | 604/228 |
| 416385 | 10/1910 | France | 604/228 |

Primary Examiner—Dalton L. Truluck
Attorney, Agent, or Firm—Fleit, Jacobson, Cohn & Price

[57] ABSTRACT

An angiographic injector has an injector portion which includes a rotating turret for housing two angiographic syringes in readiness for injection. The injector further employs a driving mechanism for connecting with and controlling the movement of a syringe plunger once one of the syringes is in place for injection. Through the use of guide means on each syringe and corresponding alignment means on a pressure jacket, the syringe is alignably and securely mounted within the pressure jacket on the rotating turret. Each syringe plunger is releasably connected to the driving mechanism for an injection operation, and released from the driving mechanism when the injection operation has been completed, such that the driving mechanism can be withdrawn from the syringe relative to the plunger without drawing body fluid of a patient into the syringe. Various types of plunger release mechanisms for this purpose are disclosed.

65 Claims, 21 Drawing Figures

ANGIOGRAPHIC INJECTOR AND ANGIOGRAPHIC SYRINGE FOR USE THEREWITH

This is a continuation-in-part of application Ser. No. 617,807, filed June 6, 1984, and now abandoned.

BACKGROUND OF THE INVENTION

1. Field of the Invention

This invention relates to the field of angiography. Angiography is the study of blood vessels with the use of x-rays while injecting an iodine-based or other fluid (contrast media) into the body through a catheter situated in a blood vessel. An angiographic injector utilizes an angiographic syringe filled with contrast media and serves to control the delivery rate, amount, pressure, etc., of the fluid being injected.

2. Background of the Prior Art

Although there are many angiographic injectors (see U.S. Pat. Nos. 4,006,736, for example) and many angiographic syringes commercially available in the world market, there are certain areas where improvements or advances can be made. For example, there is no known multiple-syringe angiographic injector permitting the syringe plunger to be disengaged without retracting the plunger back through the syringe and hence possibly drawing blood and other fluid from the patient. Also, the design of the prior art syringe may not maximize the purging of air from within because of the taper angle of the syringe's end. Finally, the length of the discharge extension in prior art syringes does not permit efficient handling of the syringe by the surgeon.

Accordingly, it is an object of this invention to provide an angiographic injector which utilizes a means for engaging an angiographic syringe which is capable of unilaterally disengaging and retracting from the syringe plunger without drawing the plunger back through the syringe.

Another object of the invention is to provide an angiographic syringe fixedly mountable within the pressure jacket to maintain alignment between the syringe and the pressure jacket.

Yet another object of this invention is to provide an angiographic syringe which promotes improved air removal therefrom.

Still another object of this invention is to provide an angiographic syringe which increases the size of the sterile work field.

SUMMARY OF THE INVENTION

In general, an angiographic syringe includes a plunger which is advanceable through a tubular body for forcing contrast media from a discharge end of the tubular body into the vascular system of an animal in an injection operation. The plunger is advanced through the tubular body by an actuating mechanism of an angiographic injector. After the injection operation has been completed, the actuating mechanism is retractable relative to the plunger of the syringe without causing any substantial retraction of the plunger in the tubular body so as to draw body fluid of the animal into the syringe.

More specifically, the foregoing and other objects of the invention are achieved by providing a novel angiographic injector utilizing a specially adapted novel angiographic syringe. The angiographic injector has an injector portion which includes a rotating turret for housing multiple syringes in readiness for injection. The injector further employs a driving mechanism for connecting with and controlling the movement of the syringe plunger once the syringe is in place for injection. Through the use of guide means on the syringe and corresponding alignment means on the pressure jacket, the syringe is alignably and securely mounted within the pressure jacket on the rotating turret. In certain arrangements, the syringe plunger is positioned within the syringe such that when the syringe is mounted within the pressure jacket, a plunger connecting means will be properly aligned for mating with the driving mechanism. This mating occurs upon rotation of the turret into position for injection on the injector portion. Once the injection is complete, the driving mechanism may be disengaged from the plunger connecting means by rotating the driving mechanism or the syringe plunger, thereby freeing the driving mechanism from the plunger so the driving mechanism can be retracted from the syringe. In other arrangements, prealignment of the plunger and the drive mechanism, and/or rotation of either the syringe plunger or the drive mechanism to release the driving mechanism from the plunger are not necessary. A discharge extension of the angiographic syringe also has been lengthened and an intermediate portion of the syringe has been given a less severe taper.

DESCRIPTION OF THE PREFERRED EMBODIMENT

Figures 1, 7, 8:
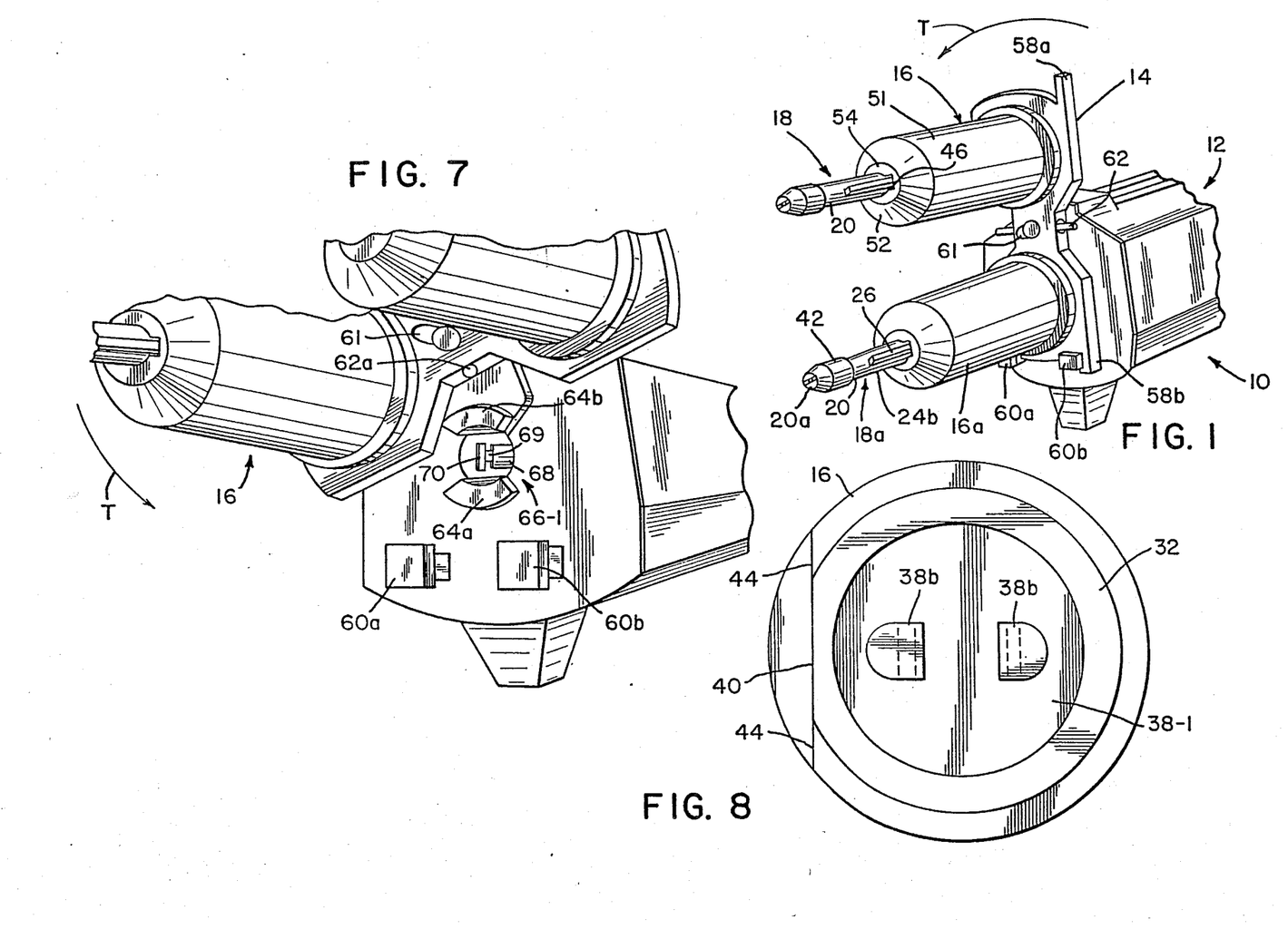
FIG. 1 is a perspective view of an angiographic injector of the present invention, illustrating an injector portion and turret assembly.
FIG. 7 is a view of the injector of FIG. 1 wherein the turret is rotated out of operative position to expose the plunger-engaging driving mechanism of the injector portion.
FIG. 8 is an end view of the syringe of FIG. 2.
Figure 2:
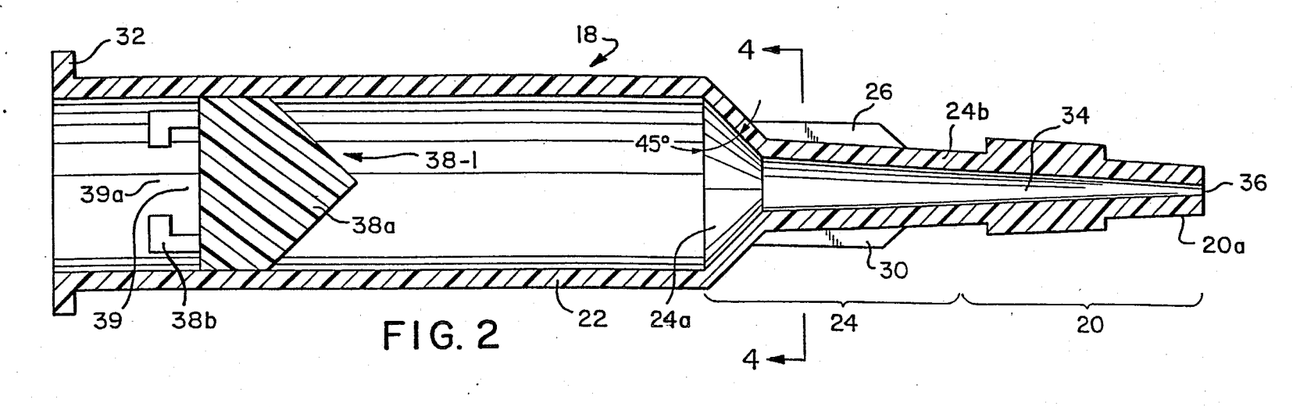
FIG. 2 is a cross-sectional view of a syringe of the present invention.

Referring now to FIGS. 1 and 2, the angiographic injector of the present invention is shown generally at 10. The injector 10 comprises an injector head portion 12 and a control unit (not shown), injector head portion 12 further comprising a turret 14 rotatably mounted about a shaft 61. Shaft 61 includes an aperture (not shown) which aligns with aperture 62a in turret 14 when turret 14 is in position for injection. Pin 62 passes through the apertures, thereby holding turret 14 in its proper position. Two pressure jackets 16 and 16a are fixed in turret 14 and house respective syringe cartridges 18 and 18a.

The syringe 18 comprises an elongated tubular body 22 and a coaxial discharge extension 20, connected by an intermediate portion 24. The tubular body 22 has a circular, outwardly extending flange 32 on one end, as well as a plunger 38-1 slideably positioned within the tubular body 22. Flange 32 serves as an abutment face for associating with the rear portion of pressure jacket 16. Plunger 38-1 comprises a base member 38a, and two hook or lug members 38b extending therefrom; the plunger 38-1 serving to control the ejection of fluid contained within syringe 18 in a desired quantity and at a desired rate. Hook members 38b are designed to facilitate axial movement of plunger 38-1.

Intermediate portion 24 of syringe 18 is in the shape of a funnel and comprises two sections, a hollow cone 24a and a tapered neck 24b. On the surface of the tapered neck 24b are located one or more guide extension tabs, three being illustrated at 26, 28 and 30. Extending axially from the tapered neck 24b is discharge extension 20 which includes a nozzle 20a, and terminates in discharge outlet 36. Discharge extension 20 serves as a guide means and provides an attachment point for connector 42 which engages with a catheter (not shown). The configuration of the nozzle 20 a of discharge extension 20 corresponds with generally accepted taper lengths and angles as described in ASA Standard Z-1955 so as to be mateable with conventional catheters. Inner passageway 34 within extension 20 can be generally cylindrical, and provides communication between discharge outlet 36 and the interior of tubular body 22.

In an effort to improve the air removal capability of syringe 18, hollow cone 24a has a taper angle ranging between 40° and 50°, as compared to the 30° angle of conventional prior art syringes. In the illustrated embodiment, cone 24a has a 45° taper angle so as to compromise between maximum air removal and manufacturing ease. Similarly, plunger 38-1 has a taper angle corresponding to that of hollow cone 24a. In addition, the combined length of tapered neck 24b and discharge extension 20 ranges between $2\frac{7}{8}$ inches and $3\frac{1}{2}$ inches, thereby providing the physician with a larger sterile work field. In the preferred embodiment, this combined length is set at $3\frac{1}{4}$ inches so as to compromise between maximum strength and length of tapered neck 24b and discharge extension 20, and manufacturing ease.

Figure 3:
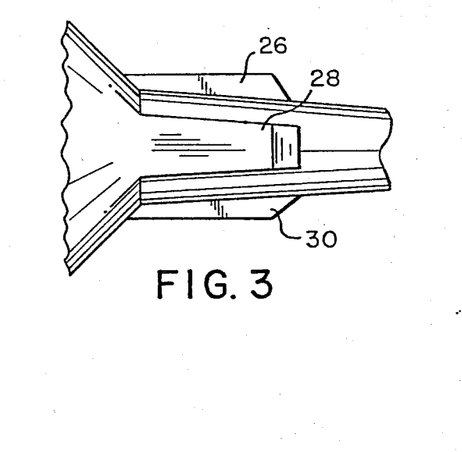
FIG. 3 is a sectional plan view of a tapered neck portion of the syringe of FIG. 2.
Figure 4:
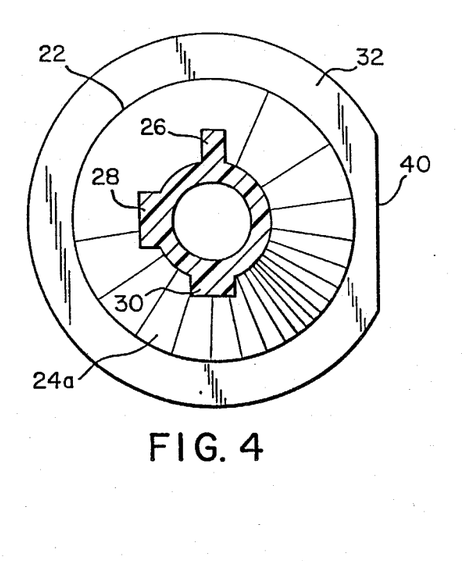
FIG. 4 is a transverse cross-sectional view taken along line 4—4 of FIG. 2.

FIGS. 3 and 4 illustrate more clearly the features and disposition of guide extensions 26, 28 and 30. In essence, guide extensions 26, 28 and 30 are raised portions of syringe 18 which extend from the end of hollow cone 24a to approximately the middle of tapered neck 24b. Although preferably made of the same material as syringe 18 and integrally formed therewith, guide extensions 26, 28 and 30 may be made of other types of plastic or suitable materials, syringe 18 preferably being formed from a relatively rigid, translucent plastic material. While the preferred embodiment employs three guide extensions 26, 28 and 30, more or less may be used. Also, the extensions may be identical, or they may be of different dimensions. For example, as shown, side guide extension 28 is larger in width but smaller in height than either top guide extension 26 or bottom guide extension 30. It also should be noted that located on the flange 32 of tubular body 22 is an alignment edge 40 which is in line with guide extension 28.

Figure 5:
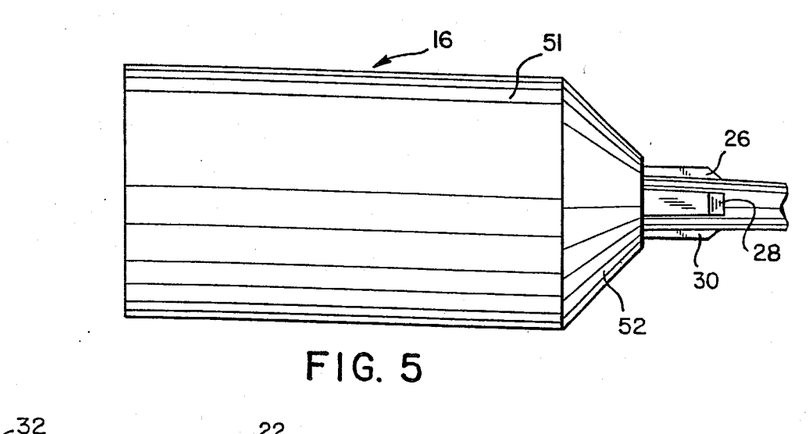
FIG. 5 is a side view of a pressure jacket and syringe assembly of the present invention.
Figure 6:
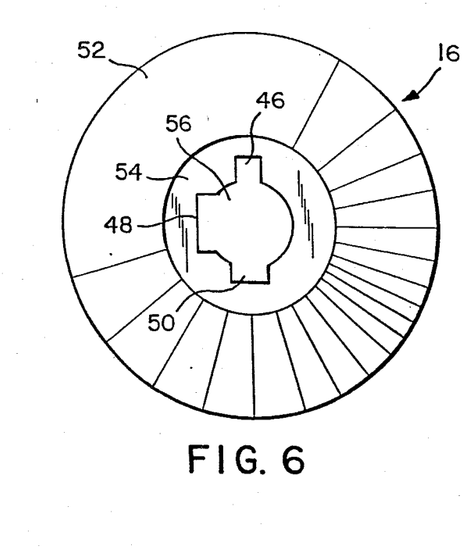
FIG. 6 is a front view of the pressure jacket of FIG. 5.

Alignment edge 40 is used to facilitate assemblage of syringe 18 with pressure jacket 16, as shown in FIGS. 5 and 6. Typically, syringe 18 is used together with pressure jacket 16 as a single, functional unit used in conjunction with an angiographic injector. In particular, pressure jackets 16 and 16a are securely and alignably mounted within the turret 14 so as to provide a means for mounting syringes 18 and 18a on turret 14 for injection. Pressure jacket 16 has a hollow body portion 51, which is substantially the same length as tubular body 22 of syringe 18, and a conical nose section 52, which is designed to fit over the hollow cone section 24a of syringe 18. At the end of conical nose section 52 is end face 54 which has guide extension notches or slots 46, 48 and 50 formed therein. Guide extension notches 46, 48 and 50 correspond to and are substantially of the same dimensions as guide extensions 26, 28 and 30, respectively. While the preferred embodiment employs three guide extension notches 46, 48 and 50, more or less may be used.

Located on the opposite end of pressure jacket 16 is an alignment indicator 44 which corresponds to alignment edge 40 of syringe 18. Alignment indicator 44 is used to ensure proper alignment of guide extensions 26, 28 and 30 with guide extension notches 46, 48 and 50 as syringe 18 is placed into pressure jacket 16. Once within pressure jacket 16, the tubular body 22 and hollow cone 24a portions of syringe 18 are completely enveloped by pressure jacket 16, while tapered neck 24b and discharge extension 20 protrude through the end face opening 56 so as to facilitate connection with a catheter. Being arranged in this manner, guide extensions 26, 28 and 30 prevent syringe 18 from rotating within pressure jacket 16 and serve to align syringe 18 with both pressure jacket 16 and turret 14.

Referring now to FIGS. 1 and 7, the two-syringe turret mechanism will be described in further detail. Turret 14, which houses pressure jackets 16 and 16a and syringes 18 and 18a is equipped with two projecting stops 58a and 58b. Fixed to the injector portion 12 are abutment members 60a and 60b adapted to associate with the stops 58a and 58b, respectively. The association between the stops 58a and 58b and the abutment members 60a and 60b limits the rotation of turret 14 from the position illustrated in FIG. 1 to the position which would be achieved by rotating turret 14 in the direction of arrow T. Therefore, once syringe 18a is in position for injection as shown in FIG. 1, turret 14 can only turn in the direction of arrow T until stop 58a associates with abutment member 60a, thereby ending rotational movement of turret 14 and aligning syringe 18 for injection.

FIG. 7 illustrates the positions of turret 14 achievable upon partial rotation in the direction of arrow T from the position shown in FIG. 1. In this intermediate position, a driving mechanism, shown generally at 66-1 in its fully retracted position, is exposed. Driving mechanism 66-1 includes a base portion 68, a stem 69 and a rectangular head 70 extending from the base portion 68 and integrally formed therewith. In this embodiment, as seen best in FIG. 9, plunger hook members 38b are L-shaped and are disposed so as to define an aperture 39 therebetween and an access slot 39a communicating with the aperture 39. This aperture 39 and access slot 39a are designed to mate with the head 70 and stem 69 of driving mechanism 66-1, such that head 70 fits within the aperture 39 and stem 69 extends through the access slot 39a. Ram elements 64a and 64b are integral with and extend from the main surface of the driving mechanism. This piston and ram arrangement is motor driven by a mechanism mounted in injector head 12, and has the same physical and operational characteristics as its counterpart disclosed in U.S. Pat. No. 4,006,736. Therefore, its configuration and operation will not be discussed in detail.

In operation, and referring now to FIGS. 1 and 7-10, syringes 18 and 18a are secured in pressure jackets 16 and 16a, respectively, by aligning syringe alignment edge 40 with pressure jacket alignment indicator 44 upon insertion of syringes 18 and 18a. By effecting such alignment, guide extensions 26, 28 and 30 pass through notches 46, 48 and 50, respectively, thereby holding syringes 18 and 18a in alignment within pressure jackets 16 and 16a.

The proper alignment of syringes 18 and 18a and pressure jackets 16 and 16a is of critical importance because of the operational characteristics of the driving mechanism 66-1. Specifically, syringe plunger hook members 38b must be in proper position to mate with the head 70 of driving mechanism 66-1.

FIG. 8 is a rear view of the syringe 18 illustrating the proper alignment of the plunger 38-1 therein. During manufacture of syringe 18, plunger 38-1 is disposed within syringe 18 such that hook members 38b extend in a predetermined relationship with the alignment edge 40 and hence with guide extensions 26, 28 and 30. As illustrated, hook members 38b extend inwardly toward the center of plunger 38-1 and are perpendicular to alignment edge 40. Therefore, pressure jacket 16 must be mounted on turret 14 so as to permit alignment of head 70 and hook members 38b. In the illustrated embodiment, this alignment is achieved by mounting pressure jacket 16 on turret 14 such that alignment indicator 44 is in a horizontal disposition when turret 14 is the position shown in FIG. 1.

Figure 9:
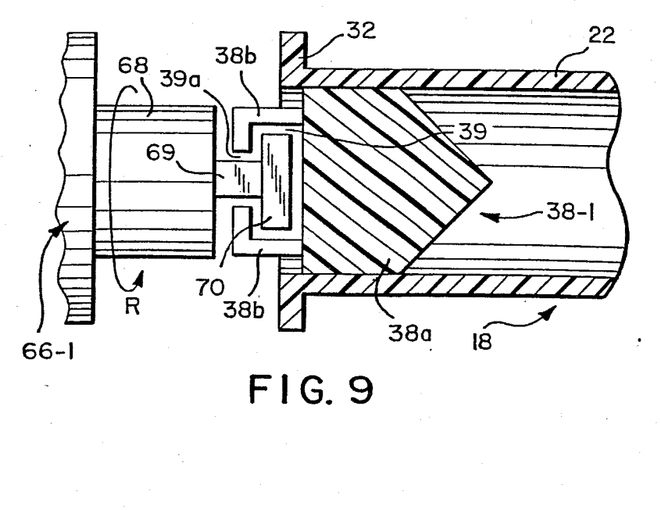
FIG. 9 is a side view of the syringe and driving mechanism as mated and prepared for injection.

Once the pressure jackets 16 and 16a are in place on turret 14, and syringes 18 and 18a secured therein, turret 14 is rotated in the direction of arrow T, as shown in FIG. 7, until projecting stop 58a engages corresponding abutment member 60a. plunger 38-1 is disposed at the end of syringe 18 with hook members 38b protruding therefrom such that hook members 38b mate or releasably interlock with head 70 of the driving mechanism 66-1 upon rotation of the turret 14, such that the hook members and the head form respective parts of a quick release driving connection between the plunger and the driving mechanism. In particular, head 70 fits into the aperture 39 formed by hook members 38b, with stem 69 extending out from the aperture 39 through access slot 39a. FIG. 9 illustrates the configuration of driving mechanism 66-1 and plunger 38-1 upon mating, focusing only on the connection between the two. As this figure illustrates, the dimensions of hook members 38b, as well as head 70 and stem 69 are critical to a proper fit. Once in the position illustrated in FIG. 9, injection may proceed through the actuation of driving mechanism 66-1, as discussed in U.S. Pat. No. 4,006,736. In particular, driving mechanism 66-1 may be moved forward, thus driving plunger 38-1 through syringe 18 and expelling air therefrom. After syringe 18 is connected to a source of contrast media, driving mechanism 66-1 may be retractd from syringe 18, thus pulling plunger 38-1 back through syringe 18 so as to draw contrast media into syringe 18. Once filled, syringe 18 is ready for injection.

Figure 10:
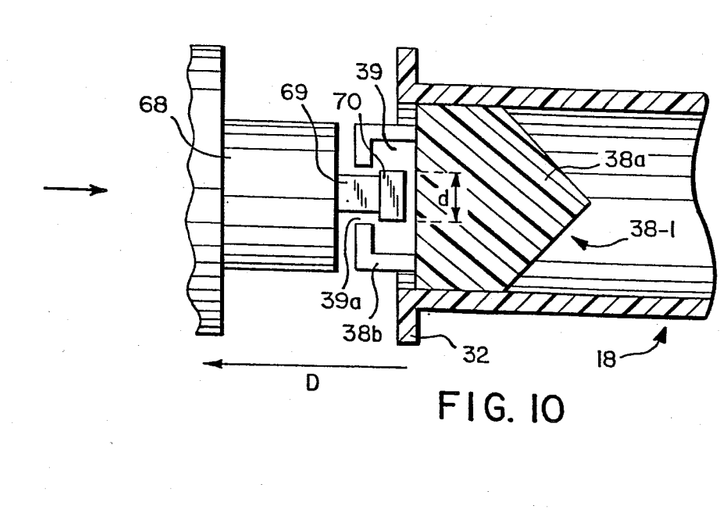
FIG. 10 is a view similar to that of FIG. 9, showing the syringe and driving mechanism in a plunger-release position as a result of rotation of the driving mechanism.

After the injection has been carried out, driving mechanism 66-1 may be disengaged from plunger 38 as shown in FIGS. 9 and 10. Without reversing its movement, driving mechanism 66-1, shown in FIG. 9, is rotated 90° in the direction of arrow R. This rotational movement results in the configuration shown in FIG. 10, wherein head 70 extends from aperture 39 on either side. As shown in FIG. 10, the depth d of head 70 must be smaller than the width of the access slot 39a so as to allow removal therefrom. Disengagement is then effected by retracting driving mechanism 66-1 in the direction of arrow D so that head 70 passes through access slot 39a. Because no reverse pressure is applied to plunger 38-1, the risks attendant to drawing the plunger 38-1 back through the syringe 18 are eliminated. Thus, the mating hook members 38b and head 70 cooperate so that the plunger 38-1 can be placed in a driven retractable state or an undriven nonretractable state of any time during the injection operation and at any position of the plunger, without substantial force being applied therebetween.

Figures 11, 12, 13, 15:
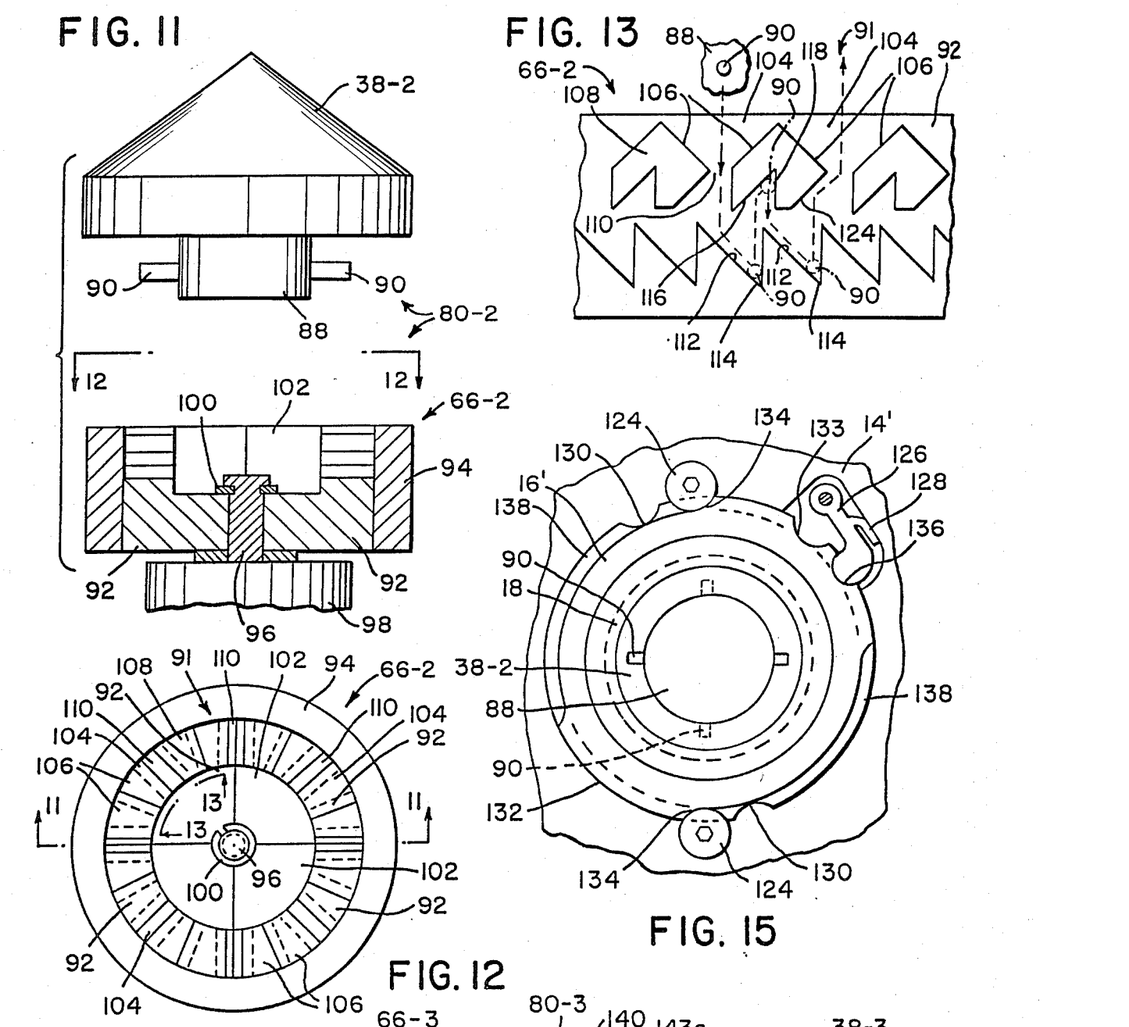
FIG. 11 is a plan view of an alternate form of rotatable-type plunger release mechanism of the present invention, in a released position, with a part of the mechanism as shown in cross-section, as viewed along the line 11—11 in FIG. 12.
FIG. 12 is a view of part of the plunger release mechanism of FIG. 11 as viewed in the direction of the arrows 12—12 in FIG. 11.
FIG. 13 is a developed pattern view of an internal cam arrangement formed in the part of the plunger release mechanism shown in FIG. 12.
FIG. 15 is a partial view of a portion of the apparatus of the present invention, demonstrating another form of plunger release mechanism which may be utilized with the internal cam arrangement shown in FIG. 14.

FIG. 11 discloses an alternate form of plunger release mechanism 80-2 of a rotatable type in which prealignment of a plunger 38-2 and a drive mechanism 66-2 are not required to connect the plunger to the drive mechanism, or to release the plunger from the drive mechanism. In this embodiment of the invention, the plunger 38-2 includes a projecting cylindrical hub 88 having a pair of laterally projecting drive lugs 90. Further, the drive mechanism 66-2 is rotatably mounted for free rotation on one end of a drive piston 98.

The drive mechanism 66-2 comprises a camming assembly 91 made up of four camming segments 92, with each segment defining a quadrant of the cylindrical camming assembly. The camming segments 92 are held together by a clamping ring 94 force-fitted and/or bonded about the periphery of the cylindrical camming assembly 91. The cylindrical camming assembly 91 is rotatably mounted for its free rotation on the drive piston 98, on a stub shaft 96 projecting from the piston, and is held on the stub shaft by a suitable C-shaped retaining clip 100. The cylindrical camming assembly 91 also includes an internal cylindrical aperture 102 for receiving the hub 88 of the plunger 38-2. The forming of the cylindrical camming assembly 91 from a plurality of parts, such as the quadrant camming segments 92, facilitates molding and/or machining of an internal camming arrangement of the assembly, as shown in FIG. 13.

Referring to FIG. 13, a camming pattern formed on the internal side of each of the quadrant camming segments 92 includes a plurality of entry-exit openings 104 arranged about the internal periphery of the cylindrical camming assembly 91. The entry-exit openings 104 are defined by inclined camming surfaces 106 of a series of camming members 108. In operation, as the drive piston 98 advances the drive mechanism 66-2 toward the plunger 38-2, each of the drive lugs 90 on the hub 88 of the plunger is received in a respective one of the entry-exit openings 104 as illustrated in FIG. 13. Each drive lug 90 is then guided by one or the other of the adjacent camming surfaces 106 into an internal passageway 110, with the drive mechanism 66-2 rotating in one direction or the other for this purpose. Each of the drive lugs 90 then engages one of a plurality of cam surfaces 112 of a rear wall 113 of an essentially saw-tooth configuration, and is guided by this cam surface into a pocket 114 of the rear wall. Continued movement of the drive piston 98 and the drive mechanism 66-2 then causes advancement of the plunger 38-2 through an associated syringe (not shown).

When the drive mechanism 66-2 then is retracted by the drive piston 98, each of the drive lugs 90 engages another internal camming surface 116 on the adjacent cam member 108 and is guided by the cam surface into a pocket 118 in the cam member. The retracting drive mechanism 66-2 then also retracts the plunger 38-2 therewith through the associated syringe to fill the syringe with a contrast media for an injection operation.

As the drive mechanism 66-2 then is again advanced by the drive piston 98, each of the drive lugs 90 engages another one of the internal camming surfaces 112 of the rear wall 113, and is guided by this camming surface into another of the internal pockets 114 in the rear wall 113. Now, continued advancement of the drive mechanism 66-2 moves the plunger 38-2 through the associated syringe to inject the contrast media from the syringe in a normal manner.

After the injection operation has been completed, the drive mechanism 66-2 is again retracted by the drive piston 98. Each of the drive lugs 90 now engages an internal camming surface 124 on the adjacent cam member 108 and is guided by this cam surface through an adjacent second one of the internal passageways 110 and out of the cylindrical camming assembly 91 through a second one of the entry-exit openings 104, to disengage the plunger 38-2 from the drive mechanism 66-2. Thus, the drive mechanism 66-2 then can be retracted without withdrawing the plunger through the associated syringe so as to draw body fluids from the patient into the syringe, as discussed hereinabove relative to the apparatus shown in FIGS. 1–10. During the above operation of the drive mechanism 66-2, the freely rotatable drive mechanism rotates relative to the plunger 38-2 as necessary in order to enable movement of the drive lugs 90 of the plunger through the drive mechanism.

Figures 14, 17, 18, 19, 20, 21:
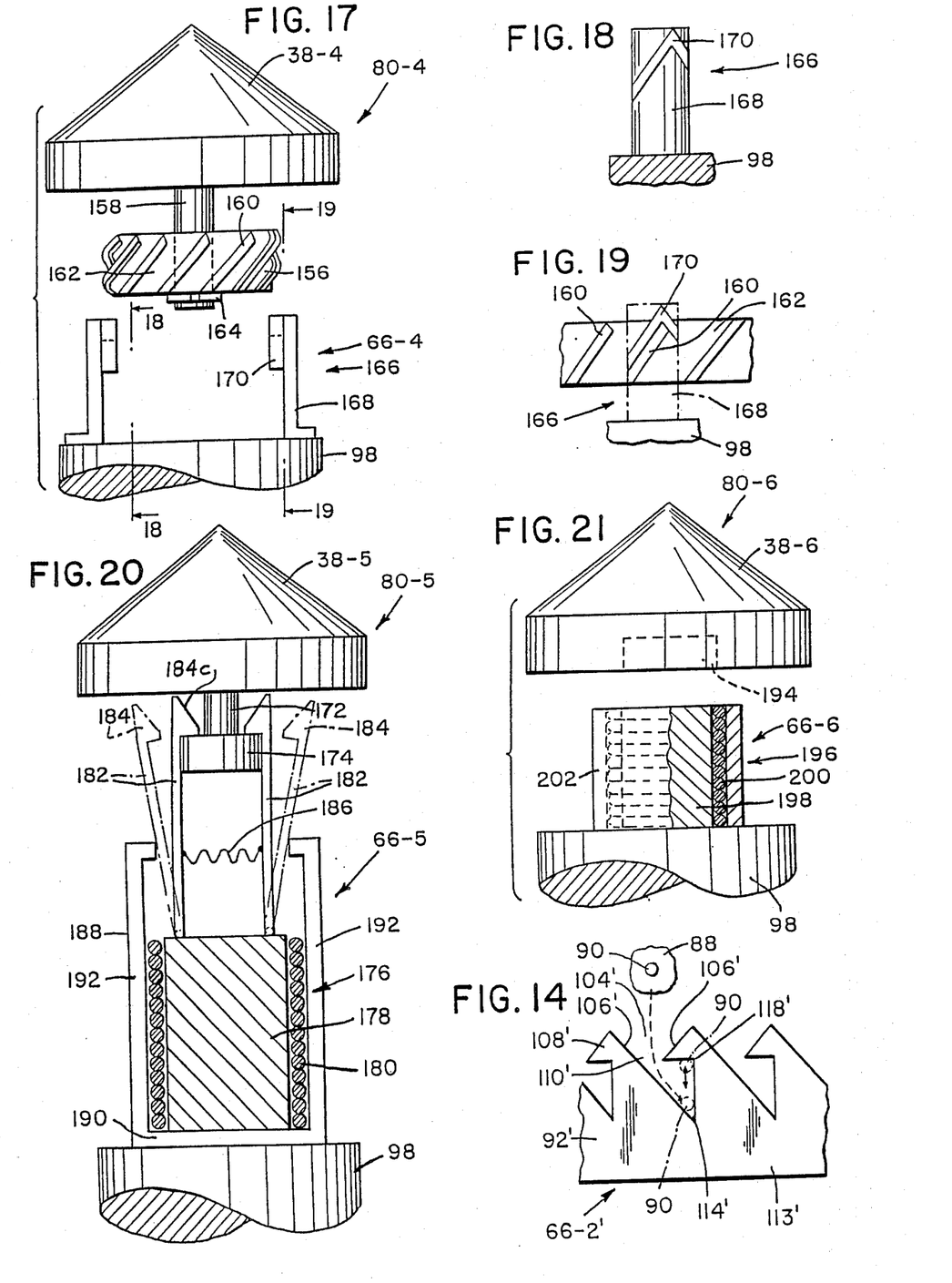
FIG. 14 is a partial developed pattern view of another form of internal cam arrangement which may be utilized in the plunger release mechanism shown in FIGS. 11, 12, and 13.
FIG. 17 is a plan view of another rotatable-type plunger release mechanism of the present invention, in a released position.
FIG. 18 is a partial view taken along the line 18—18 of FIG. 17.
FIG. 19 is a partial view illustrating the plunger release mechanism shown in FIG. 17, in a locked position as viewed along a line designated 19—19 in FIG. 17.
FIG. 20 is a plan view, partially in cross-section, of a first electromagnetic-type plunger release mechanism of the present invention.
FIG. 21 is a plan view, partially in cross-section, of a second electromagnetic-type plunger release mechanism of the present invention.

FIG. 14 discloses a partial pattern of an alternate internal camming arrangement of a drive mechanism 66-2', which may be used in place of the internal camming arrangement of the drive mechanism 66-2 shown in FIGS. 11–13. In the internal camming arrangement shown in FIG. 14, as the drive mechanism 66-2' is advanced relative to the plunger 38-2 (FIG. 11), each of the pair of laterally projecting drive lugs 90 (only one shown) on the cylindrical hub 88 of the plunger is guided by cam surfaces 106' of adjacent camming portions 108' through a passageway 110' into an internal pocket 114' formed in a rear wall portion 113' of an associated quadrant camming segment 92'. The drive mechanism 66-2' then advances the plunger through the associated syringe (not shown) as above described.

When the drive mechanism 66-2' then is retracted, each of the plunger drive lugs 90 engages in an internal pocket 118' of the adjacent camming portion 108', to retract the plunger through the syringe and to fill the syringe with contrast media as above described. Subsequently, when the drive mechanism 66-2' is again advanced for an injection operation, each of the plunger drive lugs 90 reseats in the respective internal pocket 114' and the plunger is advanced through the syringe for an injection operation. Then, when the injection operation is completed, as the drive mechanism 66-2' is again retracted by an associated drive piston (not shown), the drive piston, and thus the drive mechanism through inherent friction, also may be rotated slightly such that each of the plunger drive lugs 90 disengages from the drive mechanism through the same passageway 110' through which the drive lug became engaged with the drive mechanism.

FIG. 15 discloses an arrangement in which, rather than rotate the drive mechanism 66-2' in FIG. 14 as the drive mechanism is retracted, in order to disengage the plunger drive lugs 90 from the drive mechanism, the plunger 38-2 is rotated relative to the drive mechanism. In this connection, the embodiment of the invention shown in FIG. 15, which is a back view of a portion of a modified turret 14', includes a modified pressure jacket 16' which receives the syringe 18 shown in the embodiment of the invention shown in FIGS. 1–10. Further, the syringe 18 receives the plunger 38-2 as shown in the embodiment of the invention of FIGS. 11–13.

More specifically, the pressure jacket 16' is mounted on the modified turret 14' from the back thereof and is retained on the turret by a pair of machine screws 124 mounted on the back of the turret. The pressure jacket 16' is retained against rotation in the turret 14' by a detent member 126 pivotally mounted in a recess in the back of the turret and including a resilient integral biasing spring 128.

To mount the pressure jacket 16' on the turret 14', notches 130, formed in a peripheral flange 132 of the pressure jacket, are aligned with the machine screws 124, and a notch 133 in the peripheral flange is aligned with a detenting portion 126a of the detent member 126. The peripheral flange 132 of the pressure jacket 16' is then engaged against the turret 14' and the jacket is rotated slightly counterclockwise, as viewed in FIG. 15, so that the machine screws 124 are received in seats 134 formed in the flange, and so that the spring detent member 126 rides into a small retaining notch 136 in the flange.

When it is desired to release the plunger 38-2 from the drive mechanism 66-2' in FIG. 14 utilizing the arrangement of FIG. 15, the pressure jacket 16' is manually rotated clockwise, as viewed in FIG. 15, so that the machine screws 124 travel in respective grooves 138 formed in the peripheral flange 132 of the pressure jacket 16'. As a result, the syringe 18 in the pressure jacket 16', being in fixed relationship thereto as described herein above in the embodiment of the invention shown in FIGS. 1–10, also rotates with the jacket. Similarly, the plunger 38-2, as a result of inherent friction between the plunger and the syringe 18, is rotated with the syringe to disengage the plunger drive lugs 90 from the drive mechanism 66-2' as the drive mechanism is retracted at the conclusion of an injection operation.

Figure 16:
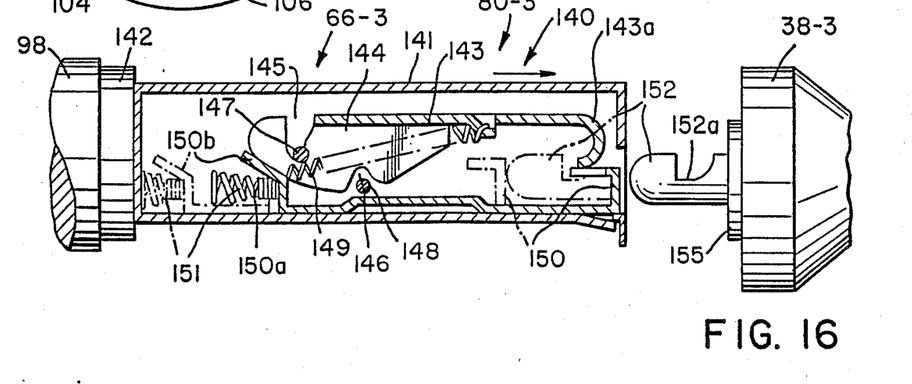
FIG. 16 is a cross-sectional side view of a reciprocable-type plunger release mechanism of the present invention.

FIG. 16 discloses a plunger release mechanism 80-3, which is of a reciprocable-type and does not require rotation of an associated plunger 38-3 or drive mechanism 66-3. The plunger release mechanism 80-3 includes a small latching device 140 of a type as disclosed in U.S. Pat. No. 2,637,576, the disclosure of which, to the extent not inconsistent with this disclosure, is hereby incorporated by reference. The latching device 140 is substantially enclosed in a box-shaped housing 141 suitably mounted on a cylindrical hub 142 of the piston rod 98. The latching device 140 includes a pivotable latch member 143 having integral depending side flanges 144 provided with upper and lower sets of notches 145 and 146 for receiving respective upper and lower pivot pins 147 and 148 mounted in side-walls (only one shown) of the housing 141. A coil spring 149 is connected at one end to a tab on the latch member 143 and at an opposite end to a tang 150a of a slide member 150 mounted on a housing bottom wall. A bumper coil spring 151 also is supported on the slide tang 150a and the slide 150 includes a pair of upwardly inclined stop lugs 150b. The plunger 38-3 includes a latch member 152 rigidly mounted thereon.

In operation, as the drive piston 98 advances, the rigid latch member 152 on the plunger 38-3 is received into an open end of the latching device housing 141, to cause the slide member 150 to move relative to the housing, to the left in FIG. 16. When a hook portion 152a on the rigid latch member 152 clears a depending hook portion 143a on the pivotable latch member 143, as illustrated by broken lines in FIG. 16, the latter latch member is pulled downward by the spring 149 about the upper pivot pin 147, into the hook portion 152a. At substantially the same time, a flange 155 of the latch member 152 is engaged by the adjacent end of the housing 141 to cause movement of the plunger 38-3 through an associated syringe (not shown).

As the drive piston 98 then retracts the latching device 140, the latch member hook portions 143a and 152a interengage so that the plunger 38-3 is retracted through the syringe to fill the syringe with contrast media in a normal manner. The retracting operation also causes the pivotable latch member 143 to be shifted slightly to the right in FIG. 16 into position for subsequent pivoting about the lower pivot pin 148.

Subsequently, when the drive piston 98 again advances the latching device 140 in an injection operation, the pivotable latch member hook portion 143a is released from the rigid latch member hook portion 152a so that the coil spring 149 now pivots the pivotable latch member 143 upward about the lower pivot pin 148, thereby returning the pivotable latch member to its inoperative position. Accordingly, when the latching device 140 is retracted by the drive piston 98 at the conclusion of the injection operation, the rigid latch member 152 releases from the latching device 140, leaving the plunger 38-3 is an advanced position in the syringe.

FIG. 17 discloses another rotatable-type plunger release mechanism 80-4 which includes a plunger 38-4 and a drive mechanism 66-4. THe plunger 38-4 includes a rotatable member 156 mounted for free rotation on a projecting stem 158. The rotatable member 156 includes a series of raised screw-type threads 160 which define a plurality of inclined channels 162 therebetween. The rotatable member 156 is retained on the stem 158 in a suitable manner, such as by a C-shaped clip 164.

The drive mechanism 66-4 includes a pair of opposed hook assemblies 166 fixedly mounted at inner ends thereof on the drive piston 98. Each of the hook assemblies 166 includes a right angle member 168 having a hook member 170 fixedly mounted thereon adjacent an outer end thereof, with the hook member being of an essentially inverted V-shaped configuration, as viewed in FIGS. 18 and 19.

In use, as the drive mechanism 66-4 is initially advanced by the drive piston 98, the hook shaped members 170 enter respective ones of the channels 162 between the screw threads 160, with the rotatable member 156 rotating to permit passage of the hook members through the channels. Eventually, outer ends of the hook assemblies 166 engage the plunger 38-4 to move the plunger through an associated syringe (not shown) in the usual manner. In the alternative, by proper dimensioning, the drive piston 98 can engage an adjacent end of the plunger stem 158 to cause this movement.

When the drive piston 98 then is retracted to retract the drive mechanism 66-4, the outer end portions of the hook members 170 engage over adjacent ones of the screw threads 160 as shown in FIG. 19, such that the plunger 38-4 then is retracted with the drive piston to fill the associate syringe with contrast media. When the drive piston 98 is then advanced in an injection operation, the plunger 38-4 again is advanced as above described. Subsequently, before the drive piston 98 is retracted at the conclusion of the injection operation, the drive piston and the hook assemblies 166 thereon may be rotated slightly to align the outer end portions of the hook members 170 with the adjacent respective channels 162, such that when the drive piston is retracted the hook members move back through the channels to disengage from the rotatable member 156 on the plunger 38-4. In the alternative, the plunger 38-4 may be mounted in a rotatable pressure jacket as disclosed by the pressure jacket 16' in FIG. 15, and the plunger 38-4 may be rotated by rotation of the pressure jacket to cause the desired disengagement.

FIG. 20 discloses a plunger release mechanism 80-5 of an electromagnetic-type, which comprises a plunger 38-5 and a drive mechanism 66-5. The plunger 38-5 includes a projecting stem 172 having an annular flange 174 fixedly mounted thereon.

The drive mechanism 66-5 includes an electromagnet 176 which comprises a ferromagnetic core 178 and a coil 180 surrounding the core. The drive mechanism 66-5 further includes a pair of opposed latch members 182 of ferromagnetic material pivotally mounted adjacent inner ends thereof on the magnetic core 178 of the electromagnet 176. The latch members 182 include outer latch portions 184 for engaging around the annular flange 174 of the plunger 38-5. The outer latch portions 184 include tapered camming surfaces 184c and are dimensioned so as to substantially fill the space between the annular flange 174 and the plunger 38-5, so that lost motion between the latch members 182 and the plunger is essentially eliminated. The latch members 182 are biased toward one another into a closed position by an interconnecting coil spring 186. The electromagnet 176 is mounted within a substantially U-shaped pole piece 188 of ferromagnetic material, having a base 190 fixed to the drive piston 98 and having a pair of projecting side legs 192.

In use, the electromagnet 176 of the drive mechanism 66-5 may be energized in preparation for an injection operation, so that the ferromagnetic latch members 182 are attracted toward the side legs 192 of the ferromagnetic pole piece 188 into open broken line positions as indicated in FIG. 20. The drive mechanism 66-5 then is advanced by the drive piston 98 until the hook portions 184 of the latch members have advanced past the annular flange 174 on the plunger 38-5, whereupon the electromagnet 176 is deenergized. The latch members 182 are then returned by the coil spring 186 to their closed position on opposite sides of the plunger flange 174 as illustrated in solid lines in FIG. 20. In the alternative, the electromagnet 176 may be left deenergized and the latch members 182 may be cammed outward by engagement of the camming surfaces 184c with the annular flange 174 as the drive mechanism 66-5 is advanced. In either instance, continued advancement of the drive mechanism 66-5 then causes the hook portions 184 of the latch members 182 to engage the plunger 38-5, to advance the plunger through an associated syringe.

Subsequently, when the drive mechanism 66-5 is retracted by the drive piston 98, the hook portions 184 on the latch members 182 engage rear portions of the plunger annular flange 174 to cause retraction of the plunger 38-5 in the syringe, to fill the syringe with a contrast media. As the drive mechanism 66-5 is then advanced by the drive piston 98 in an injection operation, the latch member hook portions 184 again engage the plunger 38-5 to advance the plunger through the syringe. At the end of the injection operation, the electromagnet 176 is again energized, causing the latch members 182 to be attracted to the side legs 192 of the ferromagnetic pole piece 188, thus releasing the plunger 38-5 from the drive mechanism 66-5. The drive mechanism 66-5 then may be retracted from the syringe relative to the plunger 38-5 by the drive piston 98.

Referring to FIG. 21, there is disclosed a second electromagnetic form of a plunger release mechanism 80-6 in which no rotation or prealignment of a plunger 38-6 and a drive mechanism 66-6 is required. In this connection, the plunger 38-6 includes a ferromagnetic member or material 194, which may include iron filings or be a permanent magnet, suitably mounted in a rear portion of the plunger. The drive mechanism 66-6 includes an electro-magnet 196 suitably mounted on the drive piston 98. The electromagnet 196 includes a ferromagnetic core 198 and a coil 200 disposed in an annular housing 202 of ferromagnetic material.

In use, as the drive mechanism 66-6 is advanced by the drive piston 98, the electromagnet 196 engages the plunger 38-6 to initially advance the plunger through an associated syringe. With the electromagnet 196 energized so as to attract the ferromagnetic member or permanent magnet 194 of the plunger 38-6 to the ferromagnetic core 198 and housing 202 of the electromagnet, when the drive mechanism 66-6 then is retracted by the drive piston 98, the plunger is also retracted with the drive mechanism to fill the syringe with a contrast media. When the drive mechanism 66-6 then is again advanced, the electromagnet 196 pushes the plunger 38-6 through the associated syringe for an injection operation. The electromagnet 196 is then deenergized or reversed in polarity, to release the ferromagnetic member or permanent magnet 194, respectively, therefrom, whereupon the drive mechanism 66-6 can be retracted from the syringe by the drive piston 98 relative to the plunger.

Although particular embodiments of the present invention have been illustrated and described, it will be apparent to those skilled in the art that various changes and modifications can be made without departing from the spirit and scope of the present invention. For example, the relative positions of the parts of the plunger release mechanisms on the plungers 38 and the drive mechanisms 66, such as the hook members 38b on the plunger 38-1, and the stem 69 and head 70 of the driving mechanism 66-1, in FIGS. 1–10, can be reversed, with the stem and head mounted on the plunger and the hook members mounted on the drive mechanism. Further, with reference to FIGS. 11–13, the camming arrangement of the drive mechanism 66-2 may be formed on external sides of the quadrant camming segments 92, with the lugs 90 on the plunger 38-2 extending rearwardly (downwardly in FIG. 11) and having laterally projecting portions extending radially inward, in a manner similar to the configuration of the hook members 38b in FIG. 2. It therefore is the intent to encompass within the appended claims all such changes and modifications that fall within the scope of the present invention.

What is claimed is:

1. An angiographic injector for injecting a contrast media from an angiographic syringe which includes a movable plunger for forcing contrast media from said syringe into the vascular system of an animal, said injector comprising:
   mounting means for supporting at least one syringe for an injection operation;
   actuating means adjacent said mounting means for controlling the movement of said plunger in said syringe;
   drive means disposed at one end of said actuating means for causing retraction of said plunger in said syringe and advancement of said plunger in said syringe to force the contrast media from said syringe in the injection operation; and
   quick release means forming respective mating parts of said plunger and said drive means for selectively placing said plunger in a driven state by said drive means such that said drive means can retract said plunger in said syringe, and in an undriven state by said drive means such that said drive means can be retracted relative to said plunger without retraction of said plunger, the mating parts of said quick release means cooperating so that said plunger can be placed in its driven state or in its undriven state at any time during the injection operation and at any position of the plunger, without substantial force being applied therebetween.

2. An angiographic injector as defined in claim 1, wherein said quick release means is an interlocking mechanism which is releasable upon relative rotational movement of said drive means and said plunger.

3. An angiographic injector as defined in claim 2, wherein said quick release interlocking mechanism comprises a stem portion and a rectangular head portion connected thereto, and at least one L-shaped hook member cooperable with said stem and head portion.

4. An angiographic injector as defined in claim 1, wherein said mounting means includes first and second alignment means for cooperating with first and second guide means disposed on said at least one syringe.

5. An angiographic injector as defined in claim 1, wherein said injector includes a rotating turret for housing two syringes sequentially movable into a position for an injection operation by rotation of said turret, said turret having first and second mounting means for supporting said syringes.

6. An angiographic injector as defined in claim 5, wherein a driven state of said drive means with the syringe plunger of one of said syringes is achieved upon rotation of said turret into position for an injection operation.

7. An angiographic injector as defined in claim 1, in which said releasable means comprises:
projecting lug means on one of said plunger or said drive means for connecting said plunger to said drive means; and
cam means forming part of the other of said plunger or said drive means and cooperable with said lug means for placing said plunger in the driven state and the undriven state as said drive means reciprocates in said syringe.

8. An angiographic injector as defined in claim 7, wherein said cam means is rotatably mounted for free rotation.

9. An angiographic injector as defined in claim 8, wherein said cam means includes a series of cam surface cooperable with said lug means for placing said plunger in the driven state and the undriven state, respectively, as said drive means reciprocates in said syringe.

10. An angiographic injector as defined in claim 1, in which said releasable means comprises:
first and second latch members forming parts of said plunger and said drive means, respectively; and
a spring-biasing mechanism associated with one of said latch members for causing interconnecting and disconnecting of the latch members, to place said plunger in the driven state and the undriven state, respectively, as said drive means reciprocates in said syringe.

11. An angiographic injector as defined in claim 1, wherein said mounting means comprises a hollow pressure jacket for accepting said at least one syringe, said pressure jacket being rotatable to rotate said syringe and said plunger with said syringe, to place said plunger in the driven and the undriven state, respectively.

12. An angiographic injector as defined in claim 1, in which said releasable means comprises:
a screw-threaded member on one of said plunger or said drive means; and
latch means forming part of the other of said plunger or said drive means and cooperable with screw threads of the screw-threaded member for placing said plunger in the driven and undriven states as said drive means reciprocates in said syringe.

13. An angiographic injector as defined in claim 1, in which said releasable means comprises:
magnetic means for placing said plunger in the driven and undriven states.

14. An angiographic injector as defined in claim 1, in which said releasable means comprises:
a circular flange on one of said plunger or said drive means;
ferromagnetic latch means forming part of the other of said plunger or said drive means and movable between latched and unlatched positions with respect to said circular flange, for placing said plunger in the driven and undriven states, respectively; and
selectively operable electromagnetic means forming part of one of said plunger or said drive means, for selectively moving said latch means between the latched and unlatched positions.

15. An angiographic injector as defined in claim 1, in which said releasable means comprises:
ferromagnetic means mounted on one of said plunger or said drive means; and
selectively operable electromagnetic means forming part of the other of said plunger or said drive means and cooperable with said ferromagnetic means to place said plunger in the driven and undriven states.

16. An angiographic injector as defined in claim 1, wherein said at least one syringe or said mounting means includes at least one guide extension tab receivable in a guide slot in the other of said syringe or said mounting means.

17. An angiographic injector as defined in claim 16, wherein said at least one syringe includes a straight alignment edge disposed on a flange of said syringe in a preselected relationship to said guide extension tab and said slot.

18. An angiographic injector as defined in claim 17, wherein said quick release means comprises a stem portion and a rectangular head portion connected thereto, and at least one L-shaped hook member cooperable with said stem and head portion.

19. An angiographic syringe for use in combination with an angiographic injector in which at least one syringe can be supported for an injection operation, said angiographic injector including drive means for effecting an injection operation, said syringe comprising:
a tubular body having a discharge end;
a plunger movably positioned in the tubular body, said plunger being retractable in said tubular body to draw contrast media into said syringe for the injection operation and being advanceable through said tubular body for forcing the contrast media from the discharge end of said tubular body in the injection operation; and
quick release means disposed at one end of said plunger for forming a part of a releasable drive connection between said drive means of said angiographic injector and said plunger such that said drive means can selectively be drivingly connected with said plunger to enable retraction of said plunger in said tubular body and to enable advancement of said plunger in said tubular body to force the contrast media from the discharge end of said tubular body in the injection operation, said quick release means being selectively releasable from said plunger at any time during the injection operation and at any position of the plunger, without substantial force being applied thereto, such that said drive means can be retracted relative to said plunger in said tubular body after the injection operation has been completed, without retraction of said plunger.

20. An angiographic syringe as defined in claim 19, wherein at least portions of said drive connection-forming means on said plunger and said drive means of said injector are relatively movable to establish said drive connection therebetween such that said drive means can retract said plunger in said syringe, and to release said drive connection such that said drive means of said injector can be retracted relative to said plunger.

21. An angiographic syringe as defined in claim 20, wherein at least portions of said drive connection-forming means on said plunger and said drive means of said injector are relatively rotatable to establish said drive connection therebetween and to release said drive connection such that said drive means can be retracted relative to said plunger.

22. An angiographic syringe as defined in claim 19, which further comprises:
 guide means for aligning said plunger in a preselected relationship with respect to said drive means of said injector.

23. An angiographic syringe as defined in claim 22, wherein said guide means comprises at least one guide extension tab disposed on one of said tubular body or a pressure jacket of said injector which receives said syringe for the injection operation, said at least one guide extension tab being receivable in a guide slot in the other of said tubular body or said jacket.

24. An angiographic syringe as defined in claim 23, wherein said guide means further comprises a straight alignment edge disposed on a flange on said tubular body adjacent an entrance end of said tubular body in preselected relationship to said guide extension tab or said slot.

25. An angiographic syringe as defined in claim 24, wherein said quick release means includes at least one L-shaped hook member extending from one of said plunger or said drive means and cooperable with a stem and a head portion on the other of said plunger or said drive means.

26. An angiographic syringe as defined in claim 19, wherein said syringe further comprises:
 a discharge extension; and
 an intermediate portion connecting said tubular body and said discharge extension, said intermediate portion being funneled and including a hollow cone section and tapered neck section.

27. An angiographic syringe as defined in claim 26, which further comprises guide extension tabs disposed on said tapered neck and cooperable with guide means on said angiographic injector for guiding said syringe into proper position in said injector.

28. An angiographic syringe as defined in claim 26, which further comprises a straight alignment edge disposed on an entrance end of said tubular syringe body and cooperable with guide means on said angiographic injector for guiding said syringe into proper position in said injector.

29. An angiographic syringe as defined in claim 26, wherein said drive-connection forming means comprises two L-shaped hook members extending from one of said plunger or said drive means and defining a slot and an aperture therebetween for receiving a stem and a head portion on the other of said plunger or said drive means.

30. An angiographic syringe as defined in claim 26, wherein said hollow cone is constructed with a taper of between 40° and 50°, thereby promoting improved air removal from said syringe.

31. An angiographic syringe as defined in claim 30, wherein said taper is 45°.

32. An angiographic syringe as defined in claim 26, wherein said tapered neck and said discharge extension have a combined length of between $2\frac{7}{8}$ inches and $3\frac{1}{2}$ inches, thereby providing a longer sterile work field.

33. An angiographic syringe as defined in claim 32, wherein said tapered neck and said discharge extension have a combined length of $3\frac{1}{4}$ inches.

34. An angiographic syringe as defined in claim 19, wherein the drive-connection forming means at the one end of said plunger includes at least one laterally projecting lug.

35. An angiographic syringe as defined in claim 19, wherein the drive connection includes a latch member on one of said plunger or said drive means controlled by a spring-biasing mechanism responsive to reciprocation of said injector drive means in said syringe.

36. An angiographic syringe as defined in claim 19, wherein the drive connection includes a drivingly engageable screw-threaded member on one of said plunger or said drive means.

37. An angiographic syringe as defined in claim 19, wherein the drive connection includes a circular flange on one of said plunger or said drive means.

38. An angiographic syringe as defined in claim 19, wherein the drive connection includes a magnetic means.

39. An angiographic syringe as defined in claim 38, wherein said magnetic means includes a permanent magnet on one of said plunger or said drive means.

40. An angiographic syringe as defined in claim 19, wherein said quick release means includes at least one L-shaped hook member extending from one of said plunger or said drive means and cooperable with a stem and a head portion on the other of said plunger or said drive means.

41. An apparatus for injecting a contrast media into the vascular system of an animal, said apparatus comprising:
 at least one angiographic syringe including a plunger movably positioned in said syringe for forcing a contrast media from said syringe;
 mounting means for supporting said syringe for an injection operation;
 actuating means adjacent said mounting means for controlling the movement of said plunger in said syringe;
 drive means disposed at one end of said actuating means for causing retraction of said plunger in said syringe and advancement of said plunger in said syringe to force the contrast media from said syringe in the injection operation; and
 quick release means forming respective mating parts of said plunger and said drive means for selectively placing said plunger in a driven state by said drive means such that said drive means can retract said plunger in said syringe, and in an undriven state by said drive means such that said drive means can be retracted relative to said plunger without retraction of said plunger, the mating parts of said quick release means cooperating so that said plunger can be placed in its driven state or in its undriven state at any time during the injection operation and at any position of the plunger, without substantial force being applied therebetween.

42. An apparatus as defined in claim 41, wherein said syringe includes first and second guide means for guiding said syringe into proper position in said mounting means, and said mounting means includes first and second alignment means for cooperating with said first and second guide means.

43. An apparatus as defined in claim 41, wherein said quick release means is by a releasable interlocking mechanism.

44. An apparatus as defined in claim 43, wherein said releasable interlocking mechanism comprises two L-shaped hook members extending from one of said plunger or said drive means and defining an aperture and an access slot therebetween.

45. An apparatus as defined in claim 44, wherein said releasable interlocking mechanism further comprises a stem portion and a head portion on the other of said plunger or said drive means, said head portion designed to fit within said aperture between said hook members, with said stem portion extending through said access slot.

46. An apparatus as defined in claim 43, wherein said head portion is removed from said aperture upon 90° relative rotational movement between said actuating means and said syringe, said head portion having a depth dimension and disposed so as to permit passage of said head portion through said access slot upon retraction of said actuating means from said syringe.

47. An apparatus as defined in claim 41, wherein said quick release means is a releasable interlocking mechanism which is connectable and releasable upon relative rotation of said drive means and said plunger.

48. An apparatus as defined in claim 47, wherein said releasable interlocking mechanism includes at least one projecting lug on one of said plunger or said drive means receivable in a cam member rotatably mounted for free rotation on the other of said plunger or said drive means.

49. An apparatus as defined in claim 47, wherein said releasable interlocking mechanism includes a drivingly engageable screw-threaded member on one of said plunger or said drive means.

50. An apparatus as defined in claim 47, wherein said mounting means comprises a pressure jacket for accepting said syringe, said pressure jacket being rotatably mounted on an associated support for rotating said syringe and said plunger therein, to connect and release said releasable interlocking mechanism between said plunger and said drive means.

51. An apparatus as defined in claim 41, wherein said quick release means is releasable interlocking mechanism which is connectable and releasable upon relative reciprocation of said drive means and said plunger.

52. An apparatus as defined in claim 51, wherein said releasable interlocking mechanism includes a latch member controlled by a spring-biasing mechanism responsive to reciprocation of said drive means.

53. An apparatus as defined in claim 41, wherein said quick release means is a releasable magnetic mechanism.

54. An apparatus as defined in claim 42, wherein said syringe further comprises:
   a tubular body having an outwardly extending flange at one end;
   a discharge extension;
   an intermediate portion connecting said tubular body and said discharge extension, said intermediate portion being funneled and including a hollow cone section and tapered neck section;
   said first guide means comprising guide extension tabs disposed on said tapered neck for cooperating with said first alignment means; and
   said second guide means comprising a straight alignment edge disposed on said tubular body for cooperating with said second alignment means.

55. An apparatus as defined in claim 54, wherein said mounting means comprises a pressure jacket for accepting said syringe, said pressure jacket having a conical nose section and first and second end faces, said end faces each having a circular opening; said first alignment means being disposed on said first end face and comprising guide extension notches for accepting said syringe guide extension tabs; said guide extension notches having substantially the same relative spacing as said guide extension tabs; said second alignment means being disposed on said second end face and comprising an alignment mark corresponding to said alignment edge of said syringe; said first and second alignment means being disposed for guiding said syringe into proper position in said pressure jacket, thereby permitting the passage of said guide extension tabs through said guide extension notches; and said pressure jacket being disposed to envelop said tubular body and said hollow cone section of said intermediate portion of said syringe upon insertion of said syringe into said pressure jacket in preparation for use, with said tapered neck and said discharge extension protruding through the circular opening of said first end face.

56. An apparatus as defined in claim 54, wherein said hollow cone is constructed with a taper of between 40° and 50°, thereby promoting improved air removal from said syringe.

57. An apparatus as defined in claim 54, wherein said taper is 45°.

58. An apparatus as defined in claim 54, wherein said tapered neck and said discharge extension have a combined length of between $2\frac{7}{8}$ inches and $3\frac{1}{2}$ inches, thereby providing a longer sterile work field.

59. An apparatus as defined in claim 58, wherein said tapered neck and said discharge extension have a combined length of $3\frac{1}{4}$ inches.

60. An apparatus as defined in claim 41, wherein said apparatus includes a rotating turret for housing two syringes sequentially movable into a position for an injection operation by rotation of said turret, said turret having first and second mounting means for supporting said syringes.

61. An apparatus as defined in claim 60, wherein said drive means of said actuating means establishes a releasable drive relationship with the syringe plunger of one of said syringes upon rotation of said turret into position for an injection operation.

62. An apparatus as defined in claim 41, wherein said quick release means comprises a stem portion and a rectangular head portion connected thereto, and at least one L-shaped hook member cooperable with said stem and head portion.

63. An apparatus as defined in claim 41, wherein said at least one syringe or said mounting means includes at least one guide extension tab receivable in a guide slot in the other of said plunger or said mounting means.

64. An apparatus as defined in claim 63, wherein said at least one syringe includes a straight alignment edge disposed on a flange of said syringe in a preselected relationship to said guide extension tab and said slot.

65. An apparatus as defined in claim 64, wherein said quick release means includes at least one L-shaped hook member extending from one of said plunger or said drive means and cooperable with a stem and a head portion on the other of said plunger or said drive means.

* * * * *

UNITED STATES PATENT AND TRADEMARK OFFICE
CERTIFICATE OF CORRECTION

PATENT NO.  : 4,677,980
DATED       : July 7, 1987
INVENTOR(S) : David M. REILLY et al It is certified that error appears in the above-identified patent and that said Letters Patent is hereby corrected as shown below:

IN THE CLAIMS:

Col. 13, line 19, delete "releasable" and insert --quick release--;
        line 32, delete "surface" and insert --surfaces--;
        line 37, delete "releasable" and insert --quick release--;
        line 53, delete "releasable" and insert --quick release--;
        line 62, delete "releasable" and insert --quick release--;
        line 66, delete "releasable" and insert --quick release--.

Col. 14, line 12, delete "releasable" and insert --quick release--.

Col. 17, line 18, delete "43" and insert --45--;
        line 48, after "is" insert --a--.

Signed and Sealed this

Twenty-third Day of August, 1988

Attest:

DONALD J. QUIGG

Attesting Officer          Commissioner of Patents and Trademarks